(12) United States Patent
Kobayashi

(10) Patent No.: US 8,817,946 B2
(45) Date of Patent: Aug. 26, 2014

(54) X-RAY DETECTOR AND X-RAY CT APPARATUS

(75) Inventor: Hiroyuki Kobayashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/515,869

(22) PCT Filed: Dec. 9, 2010

(86) PCT No.: PCT/JP2010/072115
§ 371 (c)(1),
(2), (4) Date: Jun. 14, 2012

(87) PCT Pub. No.: WO2011/074470
PCT Pub. Date: Jun. 23, 2011

(65) Prior Publication Data
US 2012/0257715 A1    Oct. 11, 2012

(30) Foreign Application Priority Data

Dec. 16, 2009   (JP) ................... 2009-285089
Jun. 21, 2010   (JP) ................... 2010-140061

(51) Int. Cl.
| G01T 1/20 | (2006.01) |
| A61B 6/03 | (2006.01) |
| A61B 6/00 | (2006.01) |
| A61B 6/06 | (2006.01) |
| G01T 1/29 | (2006.01) |
| G21K 1/02 | (2006.01) |
| A61B 6/04 | (2006.01) |

(52) U.S. Cl.
CPC ............ *G01T 1/2985* (2013.01); *A61B 6/42* (2013.01); *A61B 6/06* (2013.01); *A61B 6/4291* (2013.01); *A61B 6/4233* (2013.01); *G21K 1/025* (2013.01); *A61B 6/035* (2013.01); *A61B 6/5282* (2013.01); *A61B 6/0457* (2013.01); *A61B 6/032* (2013.01)
USPC ............................................. 378/19; 250/366

(58) Field of Classification Search
USPC ............................................. 378/19; 250/366
See application file for complete search history.

(56) References Cited

U.S. PATENT DOCUMENTS

| 6,396,898 B1 * | 5/2002 | Saito et al. ................... 378/19 |
| 7,492,857 B2 * | 2/2009 | Yasunaga et al. ............ 378/19 |
| 2002/0064252 A1 * | 5/2002 | Igarashi et al. ............... 378/19 |
| 2005/0117697 A1 * | 6/2005 | Yasunaga et al. ............ 378/19 |
| 2010/0239072 A1 * | 9/2010 | Kurochi ...................... 378/147 |

FOREIGN PATENT DOCUMENTS

| JP | 10-314157 | 12/1998 |
| JP | 2002-162472 | 6/2002 |
| JP | 2007-117677 | 5/2007 |

OTHER PUBLICATIONS

International Search Report in PCT/JP2010/072115.

* cited by examiner

*Primary Examiner* — Allen C. Ho
*Assistant Examiner* — Danielle Fox
(74) *Attorney, Agent, or Firm* — Cooper & Dunham LLP

(57) ABSTRACT

There are provided an X-ray detector, which can reduce the deformation of a collimator plate and can be easily processed and installed, and an X-ray CT apparatus using it. The X-ray detector includes a collimator plate, and a scintillator array, a photoelectric conversion element array and a substrate that are bonded in order from the X-ray incidence direction. The collimator plate is disposed such that one of a pair of opposite sides of the collimator plate is bonded to a lower support plate bonded on the scintillator array and the other side is bonded to an upper support plate and directions of the opposite sides are the same as a rotation axis direction of an X-ray CT apparatus in which the X-ray detector is provided.

9 Claims, 7 Drawing Sheets

X-RAY DETECTOR AND X-RAY CT APPARATUS

TECHNICAL FIELD

The present invention relates to an X-ray detector which detects X-rays and in particular, to a technique for installing an X-ray detector in an X-ray CT apparatus appropriately.

BACKGROUND ART

A collimator plate is disposed to remove excessive scattered rays, which are incident on a scintillator that receives X-rays transmitted through an object, when scanning a part of the object with an X-ray CT apparatus (refer to PTL 1).

CITATION LIST

Patent Literature

[PTL 1] JP-A-8-243098

SUMMARY OF INVENTION

Technical Problem

In PTL 1, however, collimator plates arrayed at fixed distances in the circumferential direction of rotation of the X-ray CT apparatus and pillars for fixing both sides of the collimator plates from the rotation axis direction are provided. Grooves for placing the collimator plates are engraved on the pillars in order to fix the collimator plates at two places of both the sides.

For this reason, there has been concern regarding the occurrence of artifacts on a CT image due to deformation resulting from the insufficient strength of the collimator plate against the centrifugal force generated by the rotational movement of the X-ray CT apparatus. In addition, since a ceramic material or the like is used for the pillars and it is necessary to engrave as many grooves as the collimator plates, there has been a problem in that the ease of processing is not sufficient when using a ceramic material or the like that requires advanced processing.

Therefore, it is an object of the present invention to provide an X-ray detector, which can reduce the deformation of a collimator plate and can be easily processed and installed, and an X-ray CT apparatus using it.

Solution to Problem

In order to achieve the above-described object, the present invention is an X-ray detector including a collimator plate, and a scintillator array, a photoelectric conversion element array and a substrate that are bonded in order from an X-ray incidence direction. The collimator plate is disposed such that one of a pair of opposite sides of the collimator plate is bonded to a lower support plate bonded on the scintillator array and the other side is bonded to an upper support plate opposite the lower support plate and directions of the opposite sides are the same as a rotation axis direction of an X-ray CT apparatus in which the X-ray detector is provided. In addition, a pair of fixed pillars adjacent to two sides in a direction perpendicular to one side of the collimator plate bonded to the upper support plate are provided, and at least one of the upper support plate and the lower support plate is bonded to the fixed pillar.

Advantage of the Invention

According to the present invention, it is possible to provide an X-ray detector, which can reduce the deformation of a collimator plate and can be easily processed and installed, and an X-ray CT apparatus using it.

BRIEF DESCRIPTION OF DRAWINGS

FIG. 2 is seen from the cross section a-a'.

FIG. 2 is seen from the cross section b-b'.

FIG. 8 is seen from the cross section c-c'.

FIG. 8 is seen from the cross section d-d'.

DESCRIPTION OF EMBODIMENTS

Figure 1:
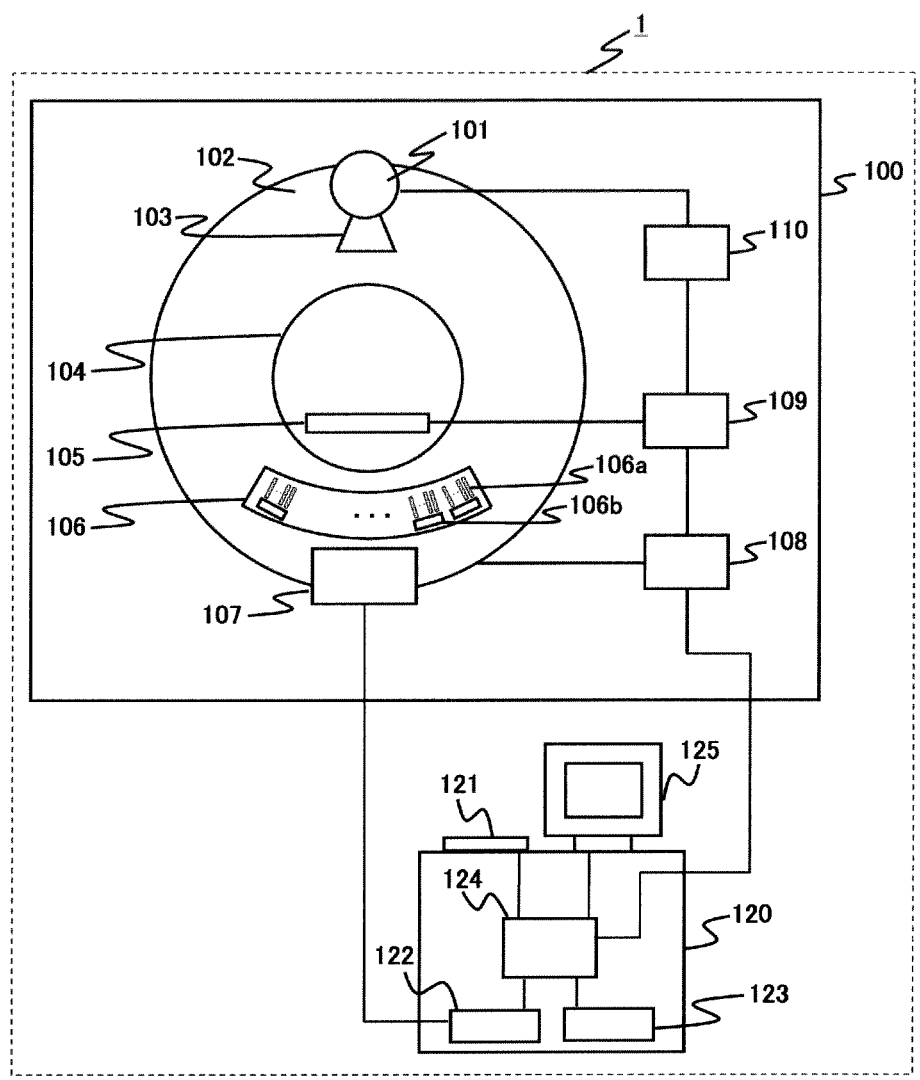
FIG. 1 is a view showing the entire configuration of an X-ray CT apparatus related to an embodiment of the present invention.

Hereinafter, an X-ray detector and an X-ray CT apparatus of the present invention will be described in detail according to the accompanying drawings. In addition, in all drawings for explaining the embodiments of the present invention, the same reference numerals are given to those with the same functions and repeated explanation thereof will be omitted.

FIG. 1 is a view showing the entire configuration of an X-ray CT apparatus to which the present invention is applied. The X-ray CT apparatus 1 includes a scan gantry unit 100 and a console 120. The scanning gantry unit 100 includes an X-ray tube 101, a rotary disk 102, a collimator for an X-ray tube 103, an X-ray detector 106, a data acquisition device 107, a bed 105, a gantry controller 108, a bed controller 109, and an X-ray controller 110. The X-ray tube 101 is a device which emits X-rays to an object placed on the bed 105. The collimator for an X-ray tube 103 is a device which restricts the radiation range of X-rays emitted from the X-ray tube 101. The rotary disk 102 includes an opening 104 through which the object placed on the bed 105 is inserted and also includes the X-ray tube 101 and the X-ray detector 106 mounted therein, and rotates around the object.

The X-ray detector 106 is a device which is disposed opposite the X-ray tube 101 and measures the spatial distribution of transmitted X-rays by detecting X-rays transmitted through the object. The X-ray detector 106 is formed by arraying a plurality of scintillator arrays 106b and a plurality of collimator plates 106a for removing excessive scattered rays, which are incident on the scintillator arrays 106b, in a rotation direction of the rotary disk 102 or arraying the scintillator arrays 106b and the collimator plates 106a in a two-dimensional direction of the rotation direction of the rotary disk 102 and the rotation axis direction. The scintillator array 106b converts detected X-rays into visible light.

The converted visible light is converted into an electric signal by a photoelectric conversion element array (not shown in the drawing in particular), and the electric signal is transmitted to the data acquisition device 107. The data acquisition device 107 is a device which acquires the amount of X-rays detected by the X-ray detector 106 as digital data. The gantry controller 108 is a device which controls the rotation of the rotary disk 102. The bed controller 109 is a device which controls the bed 105 to move up and down and back and forth. The X-ray controller 110 is a device which controls electric power input to the X-ray tube 101.

The console 120 includes an input device 121, an image operation device 122, a display device 125, a storage device 123, and a system controller 124. The input device 121 is a device for inputting the name of the object, examination date and time, scanning conditions, and the like. Specifically, the input device 121 is a keyboard or a pointing device. The image operation device 122 is a device which reconstructs a CT image by performing arithmetic processing on the measurement data transmitted from the data acquisition device 107. The display device 125 is a device which displays the CT image created by the image operation device 122. Specifically, the display device 125 is a CRT (Cathode-Ray Tube), a liquid crystal display, or the like. The storage device 123 is a device which stores data acquired by the data acquisition device 107, image data of the CT image created by the image operation device 122, and data which is stored in advance at the time of product shipment so that object information on each scan protocol and the scanning length of an object in the body axis direction are correlated (hereinafter, referred to as "storage data"). Specifically, the storage device 123 is a HDD (Hard Disk Drive) or the like.

The system controller 124 is a device which controls these devices, the gantry controller 108, the bed controller 109, and the X-ray controller 110. The X-ray controller 110 controls electric power input to the X-ray tube 101 on the basis of the scanning conditions input through the input device 121, especially, on the basis of an X-ray tube voltage, an X-ray tube current, and the like, so that the X-ray tube 101 emits X-rays to the object according to the scanning conditions. The X-ray detector 106 detects X-rays, which are emitted from the X-ray tube 101 and transmitted through the object, using a plurality of X-ray detecting elements and measures the distribution of transmitted X-rays. The rotary disk 102 is controlled by the gantry controller 108 and rotates on the basis of the scanning conditions input through the input device 121, especially on the basis of the rotation speed and the like. The bed 105 is controlled by the bed controller 109 and operates on the basis of the scanning conditions input through the input device 121, especially on the basis of the helical pitch and the like.

X-ray emission from the X-ray tube 101 and measurement of the distribution of transmitted X-rays by the X-ray detector 106 are repeated while the rotary disk 102 is rotating. As a result, projection data from various angles is acquired. The acquired projection data from various angles is transmitted to the image operation device 122. The image operation device 122 reconstructs a CT image by performing back projection processing on the transmitted projection data from various angles. The CT image obtained by reconstruction is displayed on the display device 125.

First Embodiment

Figure 3:
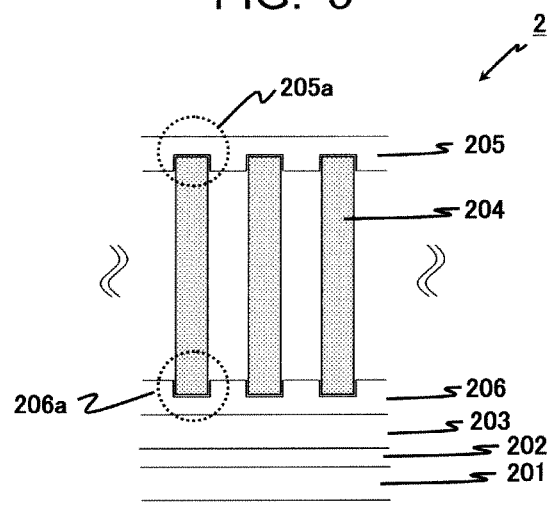
FIG. 3 is a view of an X-ray detector when
Figure 4:
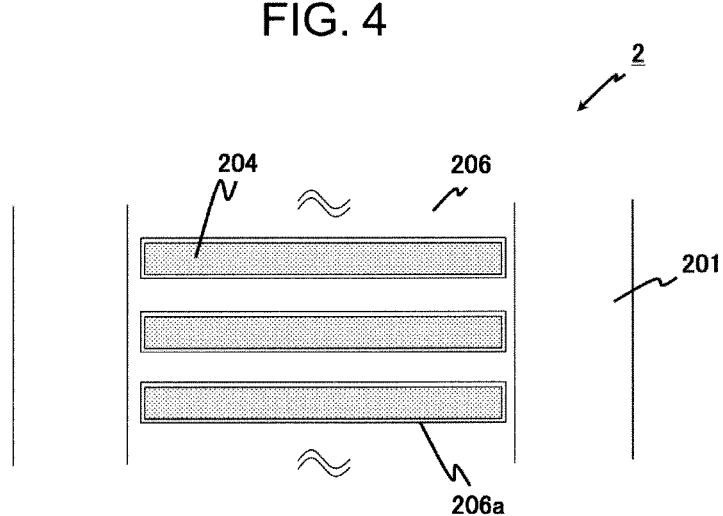
FIG. 4 is a view of an X-ray detector when

Next, a first embodiment of the present invention will be described using FIGS. 2 to 4.

Figure 2:
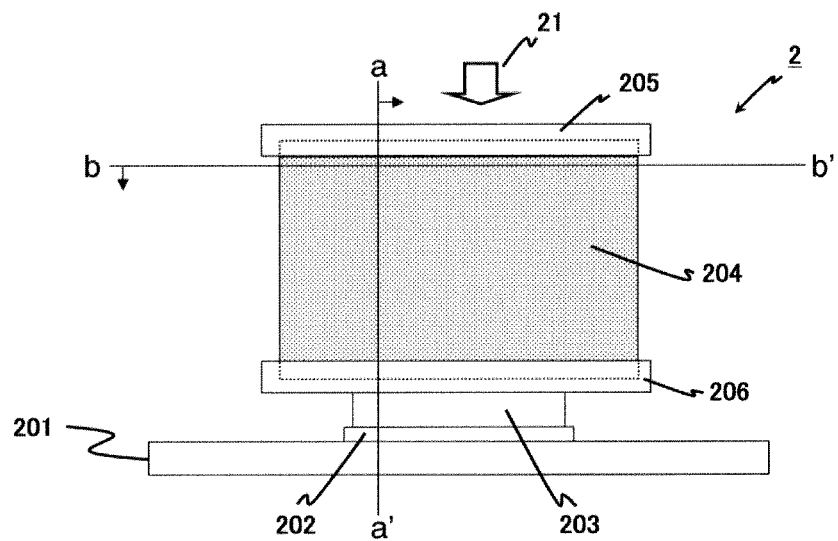
FIG. 2 is a view for explaining an X-ray detector of a first embodiment.

An X-ray detector 2 shown in FIG. 2 shows in detail a part of the X-ray detector 106 shown in FIG. 1. In addition, the X-ray detector 106 shown in FIG. 1 is a view when seen from the rotation axis direction of the X-ray CT apparatus 1, while the X-ray detector 2 shown in FIG. 2 is a view when seen from the circumferential direction of rotation of the X-ray CT apparatus 1. FIG. 3 is the X-ray detector 2 when seen in the arrow direction from the cross section a-a' shown in FIG. 2. FIG. 4 is the X-ray detector 2 when seen in the arrow direction from the cross section b-b' shown in FIG. 2.

The X-ray detector 2 of the present embodiment is provided by bonding a scintillator array 203, a photoelectric conversion element array 202, and a substrate 201 in order from the direction of the incidence of X-rays (hereinafter, an X-ray incidence direction 21).

A lower support plate 206 for fixing collimator plates 204 at approximately fixed distances in the circumferential direction of rotation of the X-ray CT apparatus 1 is provided on the surface of the scintillator array 203 facing the X-ray incidence direction 21 (hereinafter, an X-ray incidence surface). The lower support plate 206 is bonded to the X-ray incidence surface of the scintillator array 203 using an adhesive. The collimator plate 204 has a rectangular plate shape. One side of the collimator plate 204 is bonded to the lower support plate 206, and another side opposite the one side is bonded and fixed to an upper support plate 205 facing the lower support plate using an adhesive or the like.

That is, the collimator plate 204 is placed in a form in which its two sides facing each other in the same direction as the rotation axis direction of the X-ray CT apparatus 1 are interposed in the lower support plate 206 and the upper support plate 205, respectively. Although the collimator plate 204 has a rectangular shape in the present embodiment, it may have any polygonal shape with a pair of opposite sides.

A lower support plate groove 206a and an upper support plate groove 205a for positioning and placing the plurality of collimator plates 204 are provided in the lower support plate 206 and the upper support plate 205, respectively. Since the plurality of collimator plates 204 are arrayed at approximately fixed distances in the circumferential direction of rotation of the X-ray CT apparatus 1, the distance between the plurality of upper support plate grooves 205a provided in the upper support plate 205 is narrower than the distance between the plurality of lower support plate grooves 206a provided in the lower support plate 206 (not shown in the drawing in particular).

A resin material is used as a material of the lower support plate 206 and the upper support plate 205 in order to minimize attenuation of X-rays. As the resin material, there is polycarbonate or the like. By using polycarbonate injection molding by a mold, the lower support plate groove 206a and the upper support plate groove 205a can be easily formed in the lower support plate 206 and the upper support plate 205, respectively.

As described above, in the X-ray detector 2 of the present embodiment, when placing the collimator plate 204, two opposite sides of the collimator plate 204 with the same direction as the rotation axis direction of the X-ray CT apparatus 1 are disposed so as to be interposed in the lower support plate 206 and the upper support plate 205, respectively. Accordingly, since the deformation of the collimator plate 204 by the centrifugal force generated by the rotational movement of the X-ray CT apparatus can be reduced, artifacts on the CT image generated by the deformation can be reduced.

Second Embodiment

Next, a second embodiment of the present invention will be described using FIG. 5.

Figure 5:
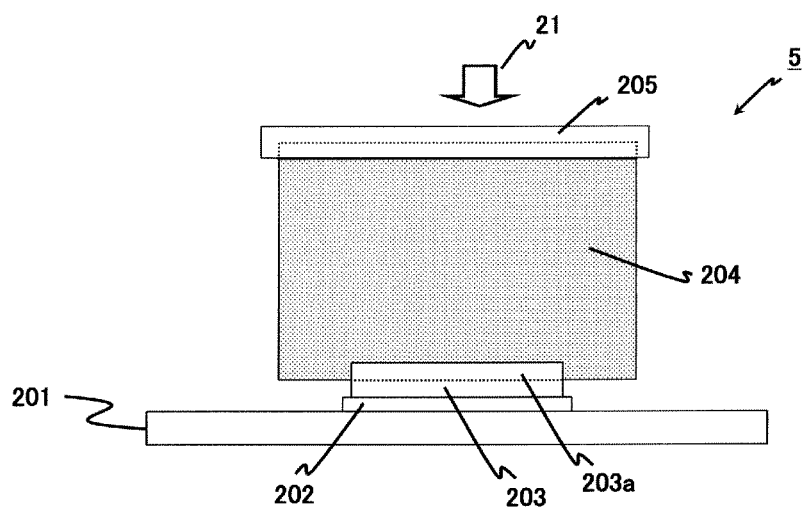
FIG. 5 is a view for explaining an X-ray detector of a second embodiment.

An X-ray detector 5 shown in FIG. 5 is a view showing a different embodiment from FIG. 2 shown in the first embodiment. A different portion from the first embodiment will be described.

Compared with the X-ray detector 2 of the first embodiment, the X-ray detector 5 of the second embodiment does not use the lower support plate 206 for placing the collimator plate 204. Instead of the lower support plate 206, a scintillator groove 203a for positioning and fixing the collimator plate 204 is provided in a part of the X-ray incidence surface of the scintillator array 203. The distance between the plurality of scintillator grooves 203a provided in the scintillator array 203 is wider than the distance between the upper support plate grooves 205a provided in the upper support plate 205 by the same reason as in the case of the first embodiment (not shown in the drawing in particular).

As described above, the X-ray detector 5 of the present embodiment does not need the lower support plate 206 since a groove is provided in a scintillator array 301 in order to place one side of the collimator plate 204 therein. Therefore, it is possible to form the lighter X-ray detector 5.

Third Embodiment

Next, a third embodiment of the present invention will be described using FIG. 6.

Figure 6:
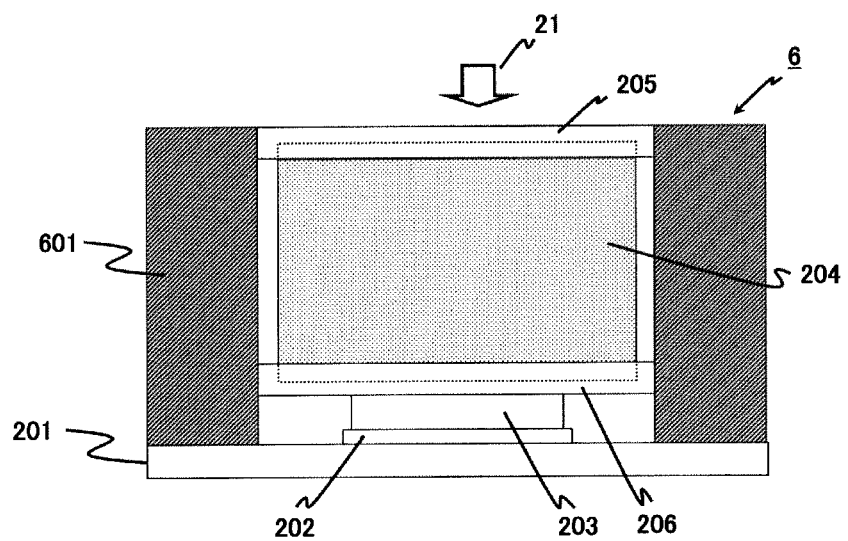
FIG. 6 is a view for explaining an X-ray detector of a third embodiment.

An X-ray detector 6 shown in FIG. 6 is a view showing a different embodiment from FIG. 2 shown in the first embodiment. A different portion from the first embodiment will be described.

Compared with the installation configuration of the collimator plate 204 of the X-ray detector 2 of the first embodiment, the lower support plate 206 and the upper support plate 205 are bonded using a pair of fixed pillars 601 which are adjacent to two sides in a direction perpendicular to one side of the collimator plate 204 bonded to the upper support plate 205, respectively, in the X-ray detector 6 of the third embodiment. In addition, the fixed pillar 601 is bonded to the substrate 201.

As described above, in the X-ray detector 6 of the present embodiment, deformation of the collimator plate 204 by the centrifugal force generated by the rotational movement of the X-ray CT apparatus can be more reduced than in the first embodiment by bonding the lower support plate 206 and the upper support plate 205 to the fixed pillar 601 bonded to the substrate 201. As a result, artifacts on the CT image generated by the deformation can be reduced.

Figure 7:
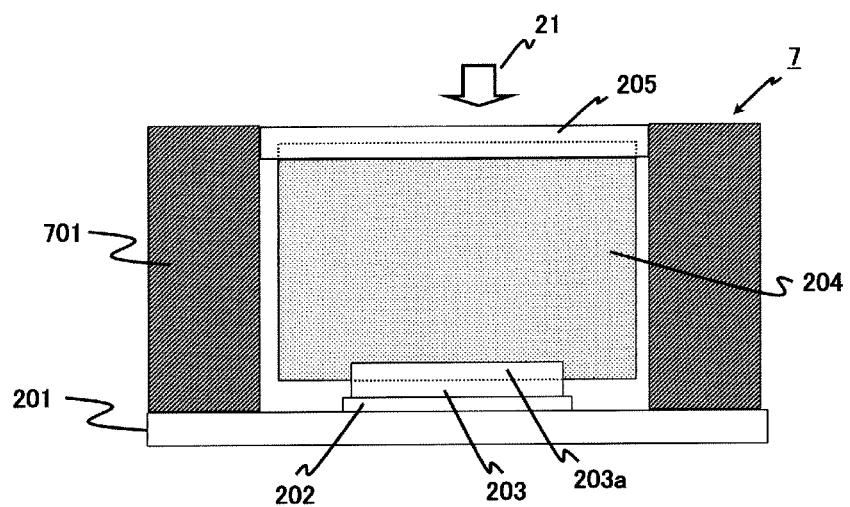
FIG. 7 is a view for explaining another X-ray detector of the third embodiment.

The present embodiment is not limited to this, and only the upper support plate 205 may be bonded using the fixed pillar 601, for example, as in an X-ray detector 7 shown in FIG. 7. In the X-ray detector 7 shown in FIG. 7, the upper support plate 205 is bonded using the fixed pillar 601 compared with the X-ray detector 5 shown in FIG. 5. In the X-ray detector 7 shown in FIG. 7, the number of components can be reduced compared with that in the X-ray detector 6. In addition, since the lower support plate 206 is not used, it is possible to eliminate attenuation of X-rays caused by the lower support plate 206.

Fourth Embodiment

Figure 9:
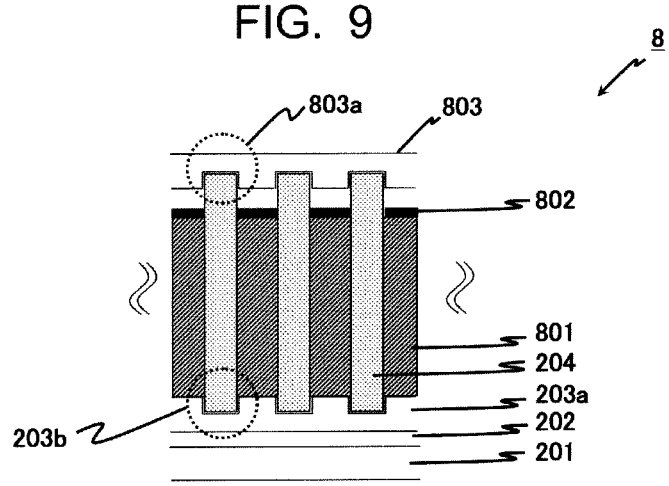
FIG. 9 is a view of an X-ray detector when
Figure 10:
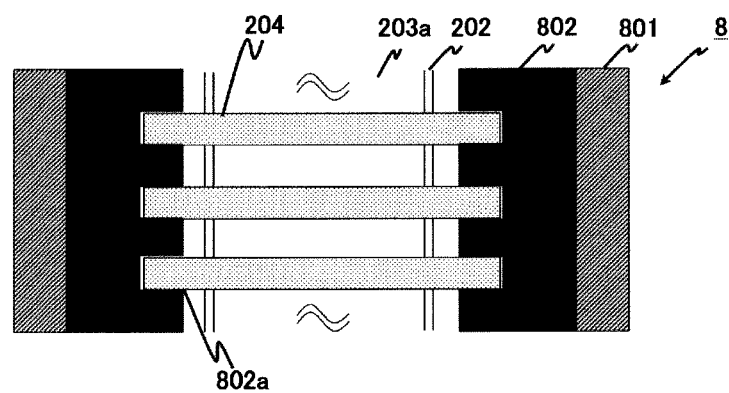
FIG. 10 is a view of an X-ray detector when

Next, a fourth embodiment of the present invention will be described using FIGS. 8 to 10.

Figure 8:
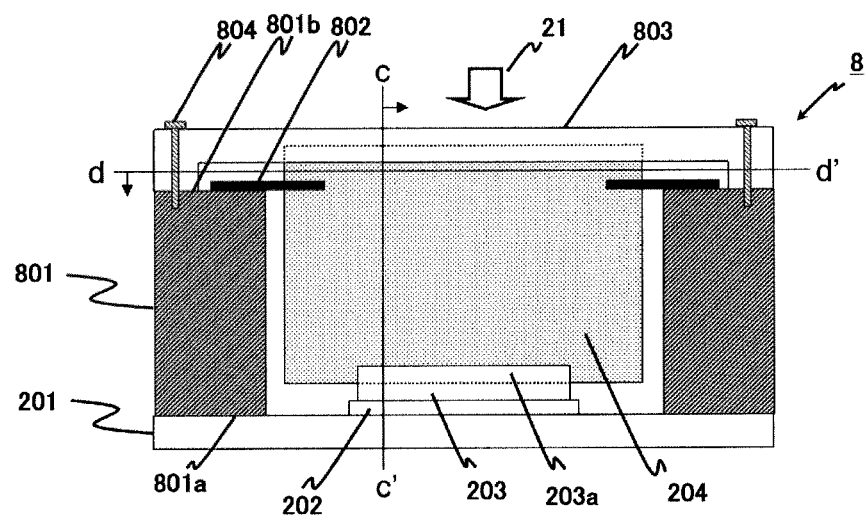
FIG. 8 is a view for explaining an X-ray detector of a fourth embodiment.

An X-ray detector 8 shown in FIG. 8 shows in detail a part of the X-ray detector 106 shown in FIG. 1. In addition, the X-ray detector 106 shown in FIG. 1 is a view when seen from the rotation axis direction of the X-ray CT apparatus 1, while the X-ray detector 8 shown in FIG. 8 is a view when seen from the circumferential direction of rotation of the X-ray CT apparatus 1. FIG. 9 is the X-ray detector 8 when seen in the arrow direction from the cross section c-c' shown in FIG. 8. FIG. 10 is the X-ray detector 8 when seen in the arrow direction from the cross section d-d' shown in FIG. 8.

The X-ray detector 8 of the present embodiment includes a comb-shaped metal plate 802, which has a comb-shaped groove 802a with a comb shape for fixing the plurality of collimator plates 204 toward the collimator plate 204, at the top 801b opposite the bottom 801a of a fixed pillar 801 provided on the substrate 201, and the collimator plate 204 is fixed by four parts of the comb-shaped metal plates 802, the scintillator groove 203a, and an upper support plate 803.

In order to form the comb-shaped groove 802a, a plurality of comb-shaped metal plates 802 are made to overlap and are then machined simultaneously by a diamond blade or a multi-wire saw. Thus, a plurality of comb-shaped metal plates 802 can be easily formed.

The comb-shaped metal plate 802 bonds a part of the side of the collimator plate 204 to the comb-shaped groove 802a while maintaining the positional relationship between grooves of the comb-shaped groove 802a and the scintillator groove 203a. Since the plurality of collimator plates 204 are radially arrayed in the circumferential direction of rotation of the X-ray CT apparatus 1 between adjacent collimator plates 204, the distance between the comb-shaped grooves 802a and the distance between the scintillator grooves 203a may be different. More specifically, the distance between the comb-shaped grooves 802a, which are located further inward with respect to the rotation axis of the X-ray CT apparatus 1 than the scintillator grooves 203a, is narrower than the distance between the scintillator grooves 203a.

Similar to the upper support plate groove 205a provided in the upper support plate 205, an upper support plate groove 803a for fixing one side of the collimator plate 204 is provided in the upper support plate 803. Accordingly, more specifically, one side of the collimator plate 204 is bonded and fixed to the upper support plate groove 803a provided in the upper support plate 803.

When placing the upper support plate 803, the upper support plate groove 803a and the collimator plate 204 are aligned after all the collimator plates 204 on the substrate 201 are bonded by the comb-shaped groove 802a and the scintillator groove 203a, and the collimator plate 204 is fixed by the upper support plate 803 so as to cover the collimator plate 204. In order to bond the upper support plate groove 803a and the collimator plate 204 to each other, it is preferable to use an adhesive or the like, which is cured at a temperature close to room temperature, so that the shrinkage of resin when cured is suppressed. In addition, the upper support plate 803 which fixes the collimator plate 204 is bonded to the top of the fixed pillar 801 with a screw 804, an adhesive, or the like.

A resin material is used as a material of the upper support plate 803 in order to minimize attenuation of X-rays. As the resin material, there is polycarbonate or the like. When forming the upper support plate groove 803a with polycarbonate, the same method as the method when forming the upper support plate groove 205a can be used.

A material with which machining accuracy is easily obtained, such as ceramic or brass, is used for the fixed pillar 801. Ceramic material is light but lacks ease of processing. In the present embodiment, however, it is not necessary to form a groove, which fixes the collimator plate 204, with a ceramic material for each collimator plate 204 even if a ceramic material is used. Accordingly, the present embodiment can be executed without reducing the ease of processing.

The present embodiment is not limited to this, and it is needless to say that the present embodiment can also be applied to a case where the lower support plate 206 is used instead of the scintillator groove 203*a* to place the collimator plate 204, for example.

As described above, in the X-ray detector 8 of the present embodiment, deformation of the collimator plate 204 by the centrifugal force generated by the rotational movement of the X-ray CT apparatus can be more reduced than in the third embodiment by fixing the collimator plate 204 from all sides by the comb-shaped metal plates 802, the scintillator groove 203*a* or the lower support plate 206, and the upper support plate 803. As a result, artifacts on the CT image generated by the deformation can be reduced.

Fifth Embodiment

Next, a fifth embodiment of the present invention will be described using FIG. 11.

Figure 11:
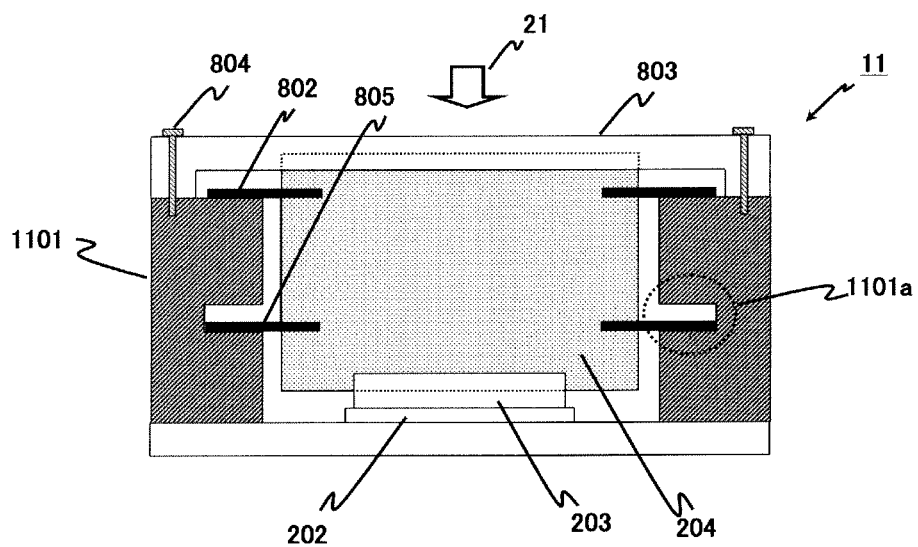
FIG. 11 is a view for explaining an X-ray detector of a fifth embodiment.

In an X-ray detector 11 shown in FIG. 11, the collimator plate 204 is fixed using a comb-shaped metal plate 805 further compared with the X-ray detector 8 shown in FIG. 8.

The comb-shaped metal plate 805 has a comb-shaped groove (not shown in the drawing in particular) with a comb shape for fixing the collimator plate 204 in the same manner as the comb-shaped metal plate 802, and its shape and material are the same as those of the comb-shaped metal plate 802. The collimator plate 204 is fixed by the comb-shaped groove of the comb-shaped metal plate 805.

The comb-shaped metal plate 805 is placed in a slit 1101*a* which is formed in the approximately middle portion of a fixed pillar 1101 so as to be approximately parallel to the substrate 201. Even if a material, such as ceramic or brass, is used for the fixed pillar 1101 in the same manner as for the fixed pillar 801, it is not necessary to form a groove corresponding to each collimator plate 204 with a ceramic material or brass. Accordingly, the present embodiment can be executed without reducing the ease of processing.

As described above, in the X-ray detector 11 of the present embodiment, deformation of the collimator plate 204 by the centrifugal force generated by the rotational movement of the X-ray CT apparatus can be reduced more than in the fourth embodiment by increasing the number of bonding places of the collimator plate 204 using the comb-shaped metal plate 805 in addition to the comb-shaped metal plate 802 so that it is fixed in a total of six places. As a result, artifacts on the CT image generated by the deformation can be reduced.

The present embodiment is not limited to this. It is also possible to provide a slit, which is formed in the same manner as the slit 1101*a*, in the fixed pillar 1101 and to increase the number of bonding places of the collimator plate 204 by placing the same comb-shaped metal plate as the comb-shaped metal plate 805 in the provided slit.

Sixth Embodiment

Next, a sixth embodiment of the present invention will be described using FIG. 12.

Figure 12:
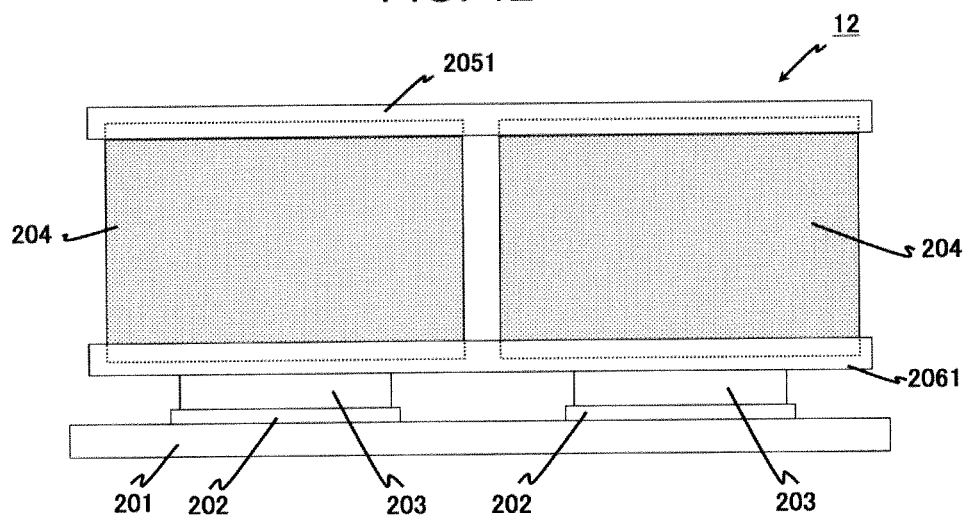
FIG. 12 is a view for explaining an X-ray detector of a sixth embodiment.

An X-ray detector 12 shown in FIG. 12 is a view showing a case where a plurality of scintillator arrays 203 and a plurality of photoelectric conversion element arrays 202 are arrayed on the substrate 201 in the rotation axis direction of the X-ray CT apparatus 1.

Here, each scintillator array 203 and each photoelectric conversion element array 202 will be described in detail. In each of the scintillator array 203 and the photoelectric conversion element array 202, elements are arrayed in 16 columns in the rotation axis direction of the X-ray CT apparatus 1, for example. By arraying a plurality of modules, for example, 16 modules on the substrate 201 with the scintillator array 203 and the photoelectric conversion element array 202, each of which includes elements in 16 columns, as one module, it is possible to form an X-ray detector having detectors in many columns, such as 256 columns. The X-ray detector 12 shown in FIG. 12 is a view when two modules are arrayed. Dividing each module is due to various limitations on the manufacture of each element.

When a plurality of modules are arrayed in the rotation axis direction of the X-ray CT apparatus 1 as described above, the collimator plate 204 is disposed for each module and a plurality of collimator plates 204 (here, two collimator plates 204) are fixed using one lower support plate 2061 and one upper support plate 2051. Since the plurality of collimator plates 204 can be fixed at once compared with the case where the collimator plate 204 is fixed using a lower support plate and an upper support plate for each collimator plate 204, the X-ray detector 12 can be easily configured.

Naturally, the collimator plate 204 may be fixed using a lower support plate and an upper support plate for each collimator plate 204.

As described above, the X-ray detector 12 of the present embodiment can be easily configured by fixing the collimator plate 204 disposed in each module using one lower support plate 2061 and one upper support plate 2051 even when a plurality of modules are arrayed in the rotation axis direction of the X-ray CT apparatus 1.

The present embodiment is not limited to this.

Figure 13:
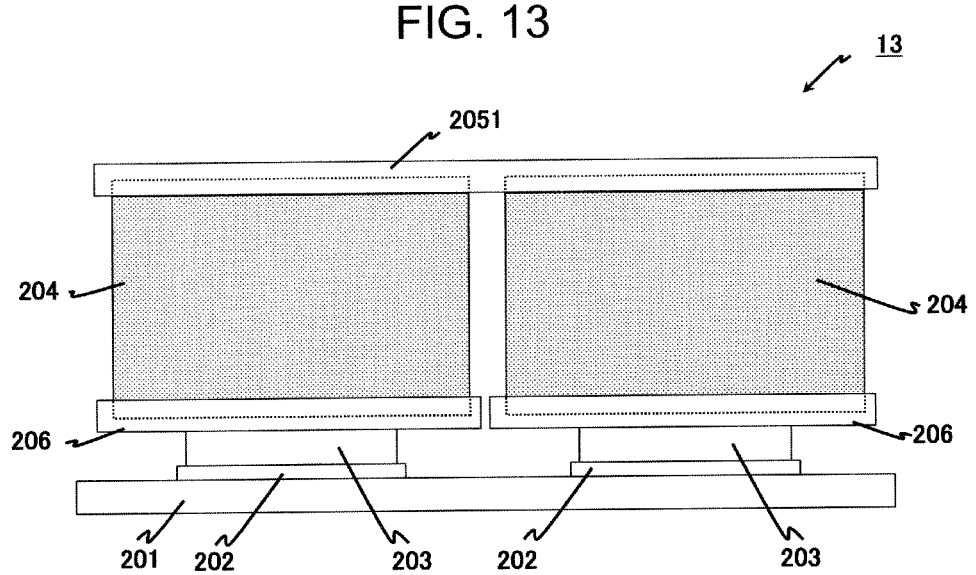
FIG. 13 is a view for explaining another X-ray detector of the sixth embodiment.

For example, as in an X-ray detector 13 shown in FIG. 13, one upper support plate 2051 which fixes the plurality of collimator plates 204 and the lower support plate 206 which is used for each collimator plate 204 may be used in combination when fixing the plurality of collimator plates 204.

DESCRIPTION OF REFERENCE NUMERALS AND SIGNS

1: X-ray CT apparatus
2, 5, 6, 8: X-ray detector
21: X-ray incidence direction
100: scan gantry unit
101: X-ray tube
102: rotary disk
103: collimator for an X-ray tube
104: opening
105: bed
106: X-ray detector
106*a*, 204: collimator plate
106*b*: scintillator array
107: data acquisition device
108: gantry controller
109: bed controller 110: X-ray controller
120: console
121: input device
122: image operation unit
123: storage device
124: system controller
125: display device
201: substrate
202: photoelectric conversion element array
203: scintillator array
203a: scintillator groove
205, 2051: upper support plate
205a: upper support plate groove
206, 2061: lower support plate
206a: lower support plate groove
301: scintillator array
601, 801: fixed pillar
801a: bottom
801b: top
802: comb-shaped metal plate
802a: comb-shaped groove
803: upper support plate
803, 803a: upper support plate groove
804: screw
805: comb-shaped metal plate
1101: fixed pillar
1101a: slit

The invention claimed is:

1. An X-ray detector comprising a collimator plate, and a scintillator array, a photoelectric conversion element array and a substrate that are bonded in order from an X-ray incidence direction, wherein in the collimator plate, one of a pair of opposite sides of the collimator plate is bonded to an X-ray incidence surface of the scintillator array and the other side is bonded to an upper support plate, and at least one place of each of two sides of the collimator plate in a direction perpendicular to the opposite sides is bonded by a comb-shaped metal plate, and wherein the comb-shaped metal plate has a groove which is parallel to the opposite sides, and wherein the comb-shaped metal plate is parallel to the X-ray incident surface of the scintillator array.

2. The X-ray detector according to claim 1,
wherein a pair of fixed pillars adjacent to two sides in a direction perpendicular to one side of the collimator plate bonded to the upper support plate are provided, and the upper support plate and the comb-shaped metal plate are bonded to the fixed pillars.

3. The X-ray detector according to claim 2, wherein a slit is provided in an approximately middle portion, in the X-ray incidence direction, of the fixed pillar so as to be approximately parallel to the substrate, and the comb-shaped metal plate is bonded to the slit.

4. An X-ray CT apparatus comprising:
an X-ray source which emits X-rays to an object;
an X-ray detector which is disposed opposite the X-ray source in order to detect X-rays transmitted through the object;
a rotary disk in which the X-ray source and the X-ray detector are mounted and which rotates around the object;
an image reconstruction device which reconstructs a tomographic image of the object on the basis of the amount of transmitted X-rays detected by the X-ray detector; and
an image display device which displays the tomographic image reconstructed by the image reconstruction device,
wherein the X-ray detector is the X-ray detector according to claim 1.

5. The X-ray CT apparatus according to claim 4, wherein the collimator plate is disposed such that one of a pair of opposite sides of the collimator plate is bonded to a lower support plate bonded on the scintillator array and the other side is bonded to an upper support plate and directions of the opposite sides are the same as a rotation axis direction of the X-ray CT apparatus.

6. The X-ray CT apparatus according to claim 5, wherein a pair of fixed pillars adjacent to two sides in a direction perpendicular to one side of the collimator plate bonded to the upper support plate are provided, and at least one of the upper support plate and the lower support plate is bonded to the fixed pillars.

7. The X-ray CT apparatus according to claim 4, wherein the collimator plate is disposed such that one of a pair of opposite sides of the collimator plate is bonded to an X-ray incidence surface of the scintillator array and the other side is bonded to an upper support plate and directions of the opposite sides are the same as a rotation axis direction of the X-ray CT apparatus.

8. The X-ray CT apparatus according to claim 7, wherein a pair of fixed pillars adjacent to two sides in a direction perpendicular to one side of the collimator plate bonded to the upper support plate are provided, and the upper support plate is bonded to the fixed pillars.

9. The X-ray detector according to claim 1, wherein the upper support plate is bonded to the collimator plates after the comb-shaped metal plate is bonded to all of the collimator plates.

* * * * *